United States Patent
Chen (10) Patent No.: US 8,916,806 B2
(45) Date of Patent: Dec. 23, 2014

(54) HEATING PAD ASSEMBLY

(71) Applicant: Chien-Chou Chen, Tainan (TW)

(72) Inventor: Chien-Chou Chen, Tainan (TW)

( * ) Notice: Subject to any disclaimer, the term of this patent is extended or adjusted under 35 U.S.C. 154(b) by 260 days.

(21) Appl. No.: 13/680,151

(22) Filed: Nov. 19, 2012

(65) Prior Publication Data

US 2014/0138374 A1 May 22, 2014

(51) Int. Cl.
  *H05B 3/06* (2006.01)
  *A61F 7/00* (2006.01)
  *H05B 1/02* (2006.01)
  *H05B 3/34* (2006.01)

(52) U.S. Cl.
  CPC ............... *A61F 7/007* (2013.01); *H05B 1/025* (2013.01); *H05B 3/342* (2013.01); *A61F 2007/0022* (2013.01); *A61F 2007/0024* (2013.01); *A61F 2007/003* (2013.01); *A61F 2007/0031* (2013.01); *A61F 2007/0042* (2013.01)
  USPC ........................... 219/527; 219/506; 219/529

(58) Field of Classification Search
  CPC  H05B 3/342; H05B 1/025; A61F 2007/0022; A61F 2007/0024; A61F 2007/0042; A61F 2007/0031
  USPC ......... 219/202, 206, 211, 497, 517, 527, 529; 607/108, 111, 112, 148; 439/37, 458, 439/607
  See application file for complete search history.

(56) References Cited

U.S. PATENT DOCUMENTS

| 3,084,241 | A | * | 4/1963 | Carrona | 219/211 |
| 4,927,366 | A | * | 5/1990 | Tommerson et al. | 439/37 |
| 5,395,399 | A | * | 3/1995 | Rosenwald | 607/108 |
| 2008/0116189 | A1 | * | 5/2008 | Fernandez et al. | 219/211 |

FOREIGN PATENT DOCUMENTS

TW           358633 M       6/2009

* cited by examiner

*Primary Examiner* — Thien S Tran (57) ABSTRACT

A heating pad assembly includes a pad and a heating plate is connected in the pad. A receptacle and a temperature control button unit are connected to the pad. The heating pad, the receptacle and the temperature control button unit are electrically connected to each other by wires. Electric power is provided to the heating pad assembly via the receptacle, and the temperature control button unit controls the operation of the heating pad. A fastening strip is cooperated with the pad to secure the pad to desired portion of the user's body.

9 Claims, 11 Drawing Sheets

FIG. 11 ature control button unit 5. Another wire is located in the pad and connected between the temperature control button unit and the heating plate.

HEATING PAD ASSEMBLY

BACKGROUND OF THE INVENTION

1. Field of the Invention

The present invention relates to a heating pad assembly, and more particularly, to a heating pad assembly suitable for being applied to different portions of user's body.

2. Description of Related Art

The conventional protection and heating pad such as waist pad, knee pad or shoulder pad as disclosed in Taiwan Utility Model Publication No. M358633 and which is positioned to the portion of the user's body to activate the blood circulation and release the period of suffering. However, the protection and heating pad is designed solely to the specific portion of the user's body so that it has a fixed shape and curvature, the user has to purchase different protection pads for different portion of the body, and this becomes an economical burden for some users. Furthermore, the multiple protection and heating pads occupy a lot of space when being stored. On the other hand, for the manufacturers, the different shapes and curvatures of the protection and heating pads require skilled workers to manufacture according to different shapes and curvatures. For the retailers, sufficient display room is needed to display these protection and heating pads.

The present invention intends to provide a heating pad assembly which can be used to different portions of the user's body.

SUMMARY OF THE INVENTION

The present invention relates to a heating pad assembly and comprises a pad and a heating plate is connected in the pad. A receptacle is connected to the pad. A wire is located within the pad and connected between the receptacle and a temperature control button unit which is fixed to the pad. Another wire is located in the pad and connected between the temperature control button unit and the heating plate.

Two fastening strips are cooperated with the pad by the connection between the hook piece and loop pieces to secure the pad to desired portion of the user's body.

The primary object of the present invention is to provide a heating pad assembly which is able to apply the heating pad to different portions of the user's body.

The present invention will become more obvious from the following description when taken in connection with the accompanying drawings which show, for purposes of illustration only, a preferred embodiment in accordance with the present invention.

DETAILED DESCRIPTION OF THE PREFERRED EMBODIMENT

Figure 1:
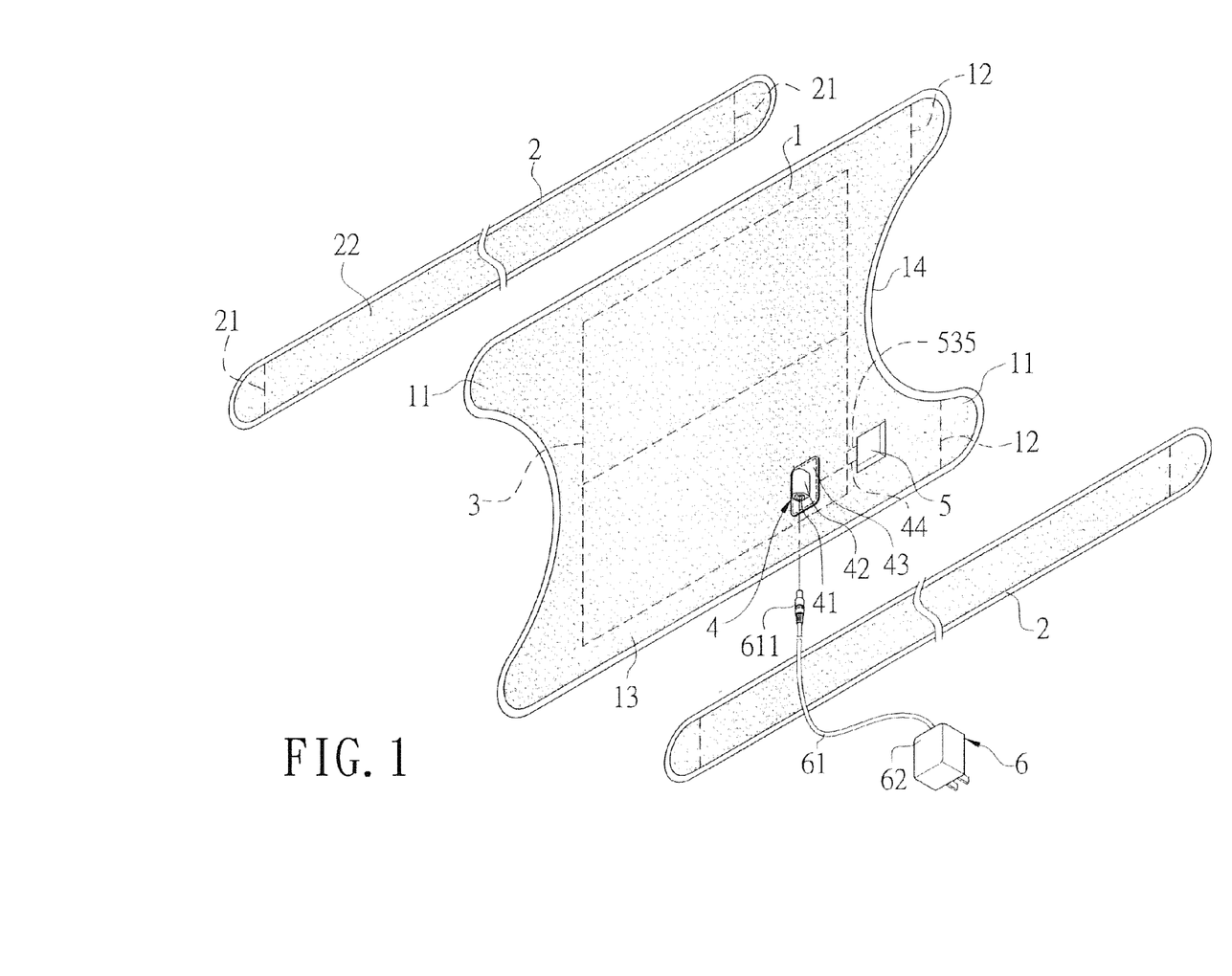
FIG. 1 is an exploded view to show the heating pad assembly of the present invention.

Referring to FIG. 1, the heating pad assembly of the present invention comprises a pad 1, at least one fastening strip 2, a heating pad 3, a receptacle 4 and a temperature control button unit 5.

The pad 1 is a rectangular pad and has four connection portions 11 extending from four corners thereof. A first hook piece 12 on the inside of the at least one of the connection portions 11 and a first loop piece 13 is connected to the whole outside of the pad 1. A recessed portion 14 is formed between the two connection portions 11 on each of the two ends of the pad 1.

There are two fastening strips 2 in this embodiment, and each of which has a second hook piece 21 on an inside of each of two ends thereof and a second loop piece 22 is connected to the whole outside of the fastening strip 2. The second hook pieces 21 are hooked to the first loop piece 13, and the first hook piece 12 is hooked to the second loop piece 22.

The receptacle 4 has a body 41 and a housing 42 mounted to the body 41. The housing 42 has a connection plate 43 extending from the periphery thereof and the connection plate 43 is sewed to the pad 1. The connection plate 43 has a hole and the wire 44 extends through the hole and is electrically connected to the body 41. The other end of the wire 44 is connected to a circuit board 531 of the temperature control button unit 5.

Figure 2:
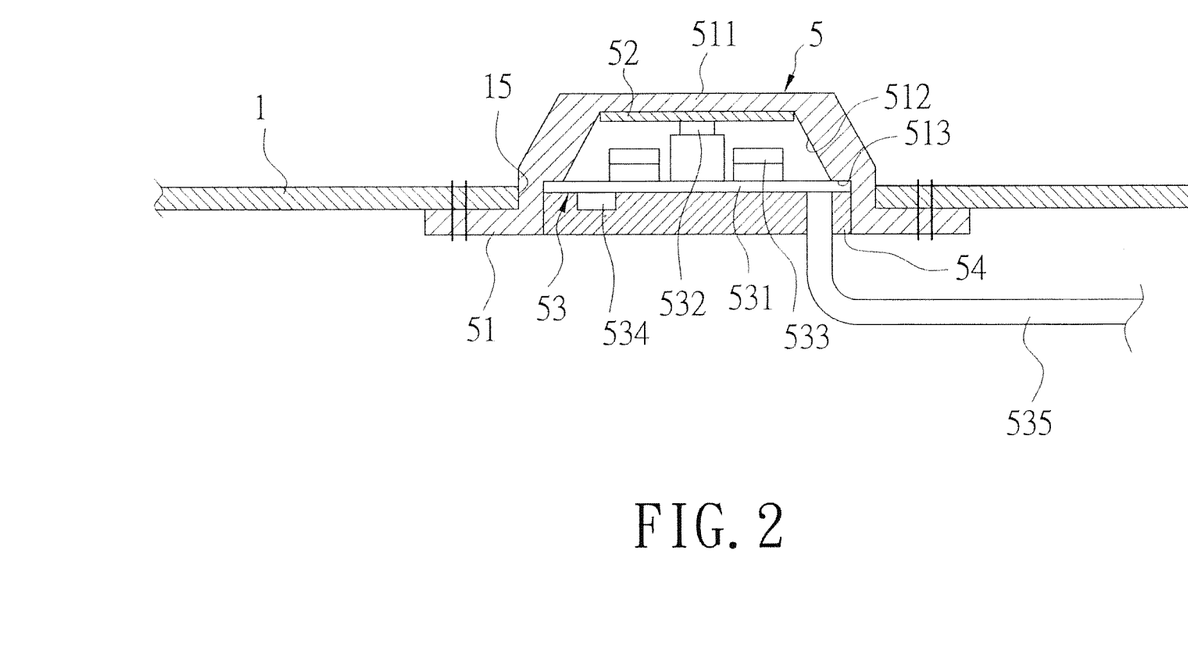
FIG. 2 is a cross sectional view of the temperature control button unit of the heating pad assembly of the present invention.

As shown in FIGS. 1 and 2, the temperature control button unit 5 has a button 51 located within the pad 1 and a pressing portion 511 protrudes from the center of the button 51. The pad 1 has an opening 15 through which the pressing portion 511 extends. The button 51 is sewed to the pad 1 along the periphery of the pressing portion 511. A recess 512 is defined in the back of the temperature control button unit 5 and located in opposite to the button 51. A stepped portion 513 is formed at the inside of the recess 512. The temperature control button unit 5 has a transparent plate 52 which is located in the recess 512 and corresponding to a control unit 53. The transparent plate 52 is positioned in the recess 512 by a fixing member 54. The control unit 53 is located in the recess 512 and has the circuit board 531 which is positioned at the stepped portion 513 and has an operation button 532 at the central portion thereof. A temperature display member 533 is located beside the operation button 532 and located corresponding to the transparent plate 52. A micro processing member 534 is connected to the circuit board 531 and electrically connected to the operation button 532 and the temperature display member 533. The temperature display member 533 is a liquid crystal display unit or digital bars or cylindrical index lights, which displays the temperature by change of colors, digits or numbers of the lights. A wire 535 and the fixing member 54 are connected to the circuit board 531. The fixing member 54 is connected to the back of the button 51 of the temperature control button unit 5 so as to position the circuit board 531, the operation button 532 and the temperature display member 533 in the recess 512. The wire 535 connected to the circuit board 531 extends beyond the fixing member 54 and located within the pad 1 so as to be connected with the heating pad 3.

Figure 3:
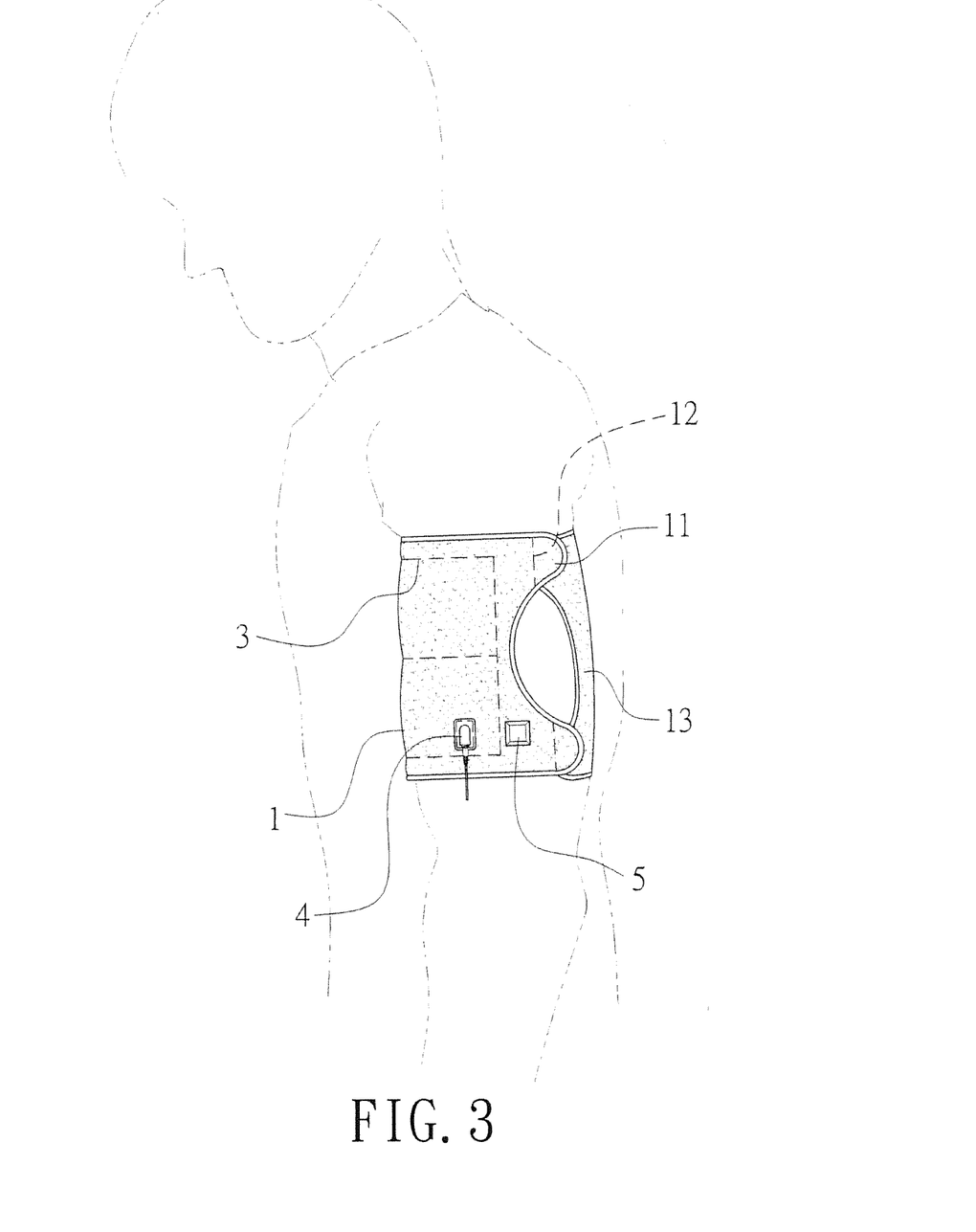
FIG. 3 shows that the heating pad assembly of the present invention is applied to the user's arm.
Figure 4:
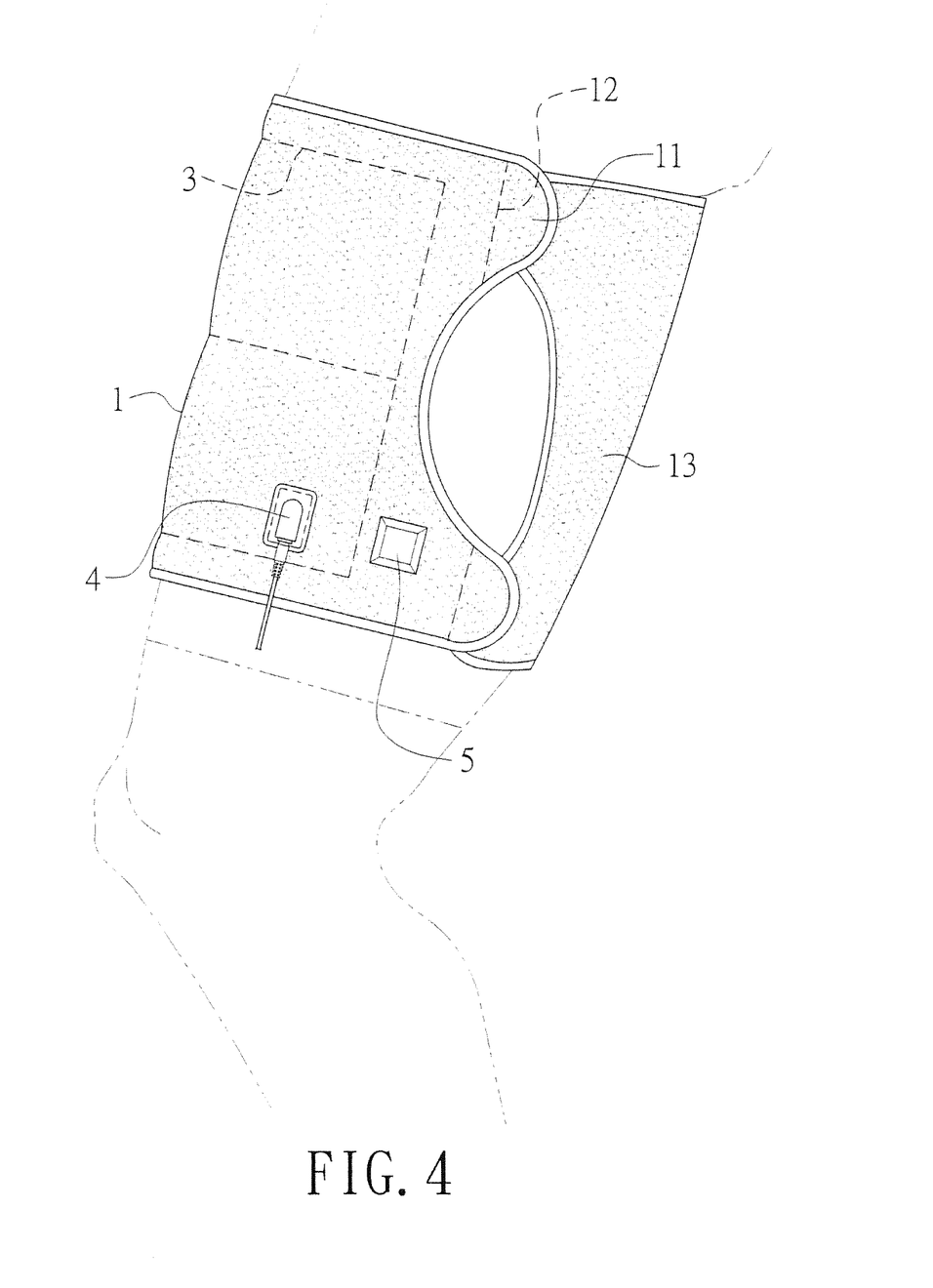
FIG. 4 shows that the heating pad assembly of the present invention is applied to the user's thigh.

As shown in FIGS. 3 and 4, when applying the heating pad assembly to the arm or the thigh, the first hook pieces 12 of the connection portions 11 on one end of the pad 1 are hooked to the first loop piece 13 on the other end of the pad 1. Because the first loop piece 13 is long and wide enough so that the first hook pieces 12 can be secured to desired positions according to the size of the applied portion of the user's body. The fastening strips 2 can be used to secure the pad 1 when the pad 1 is not well positioned to the applied portion. The second loop pieces 22 of the fastening strips 2 are connected to the first hook pieces 12 of the pad 1 first, and the fastening strips 2 are wrapped to the user's arm or thigh, and second hook pieces 21 are hooked to the first loop piece 13.

The user then connects a connector 611 of a cable 61 of a power supply 6 to the receptacle 4, and a plug 62 of the power supply 6 is connected to the city power source. The plug 62 has a transformer circuit so as to transfer the alternative current from the city power source into direct current which is sent to the receptacle 4. The wire 44 transfers the direct current to the temperature control button unit 5. The user presses the pressing portion 511 to activate the operation button 532, the micro processing member 534 of the control unit 53 is activated to pass current to the heating pad 3 via the wire 535. The heating pad 3 generates heat to warm the user's body. When the users the pressing portion 511 to activate the micro processing member 534 of the control unit 53, the temperature display member 533 is activated to display the temperature. When the user wants to adjust the temperature, he or she presses the operation button 532 by short pressing manner, the micro processing member 534 receives the short-press signal and adjusts the current to the heating pad 3. The more times the short-press is operated, the more current is provided to the heating pad 3, and the change of the temperature is displayed by the temperature display member 533. When the user wants to stop the operation of the heating pad, he or she presses the operation button 532 by one long pressing manner, the micro processing member 534 receives the long-press signal and stops the current to the heating pad 3. The change of the temperature is displayed by the temperature display member 533.

Figure 5:
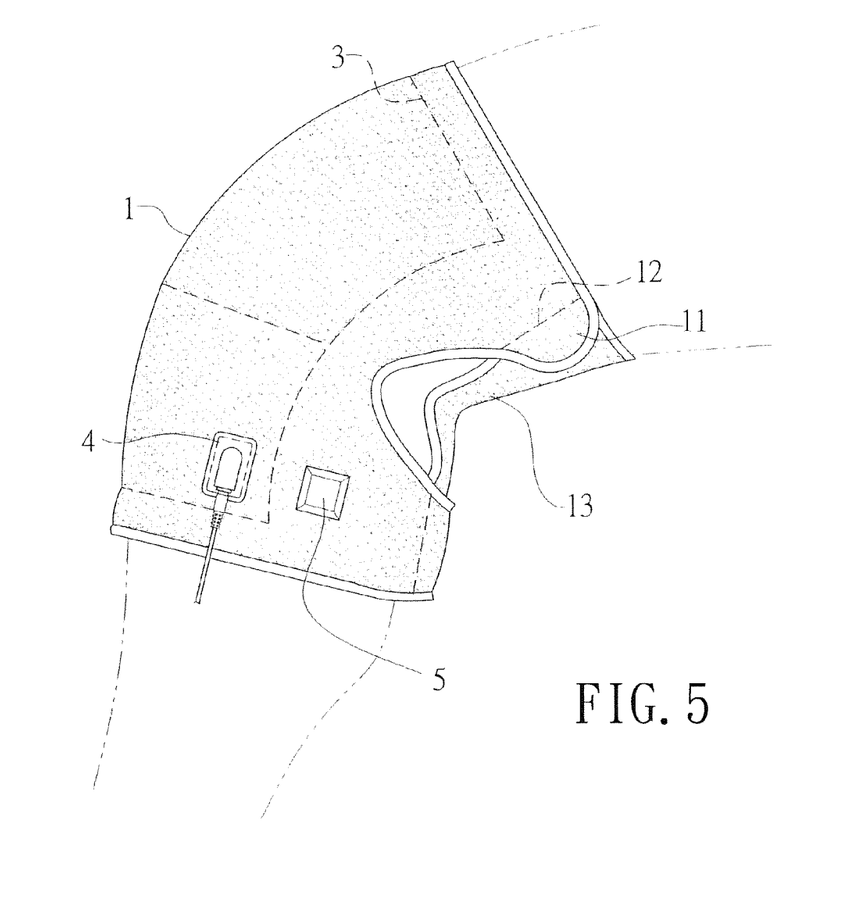
FIG. 5 shows that the heating pad assembly of the present invention is applied to the user's knee.

FIG. 5 shows that the heating pad assembly is used to the elbow and knee. The pad 1 is applied to the elbow and the knee. The first hook pieces 12 of the connection portions 11 at one end of the pad 1 are hooked to the first loop piece 13 on the other end of the pad 1.

Figure 6:
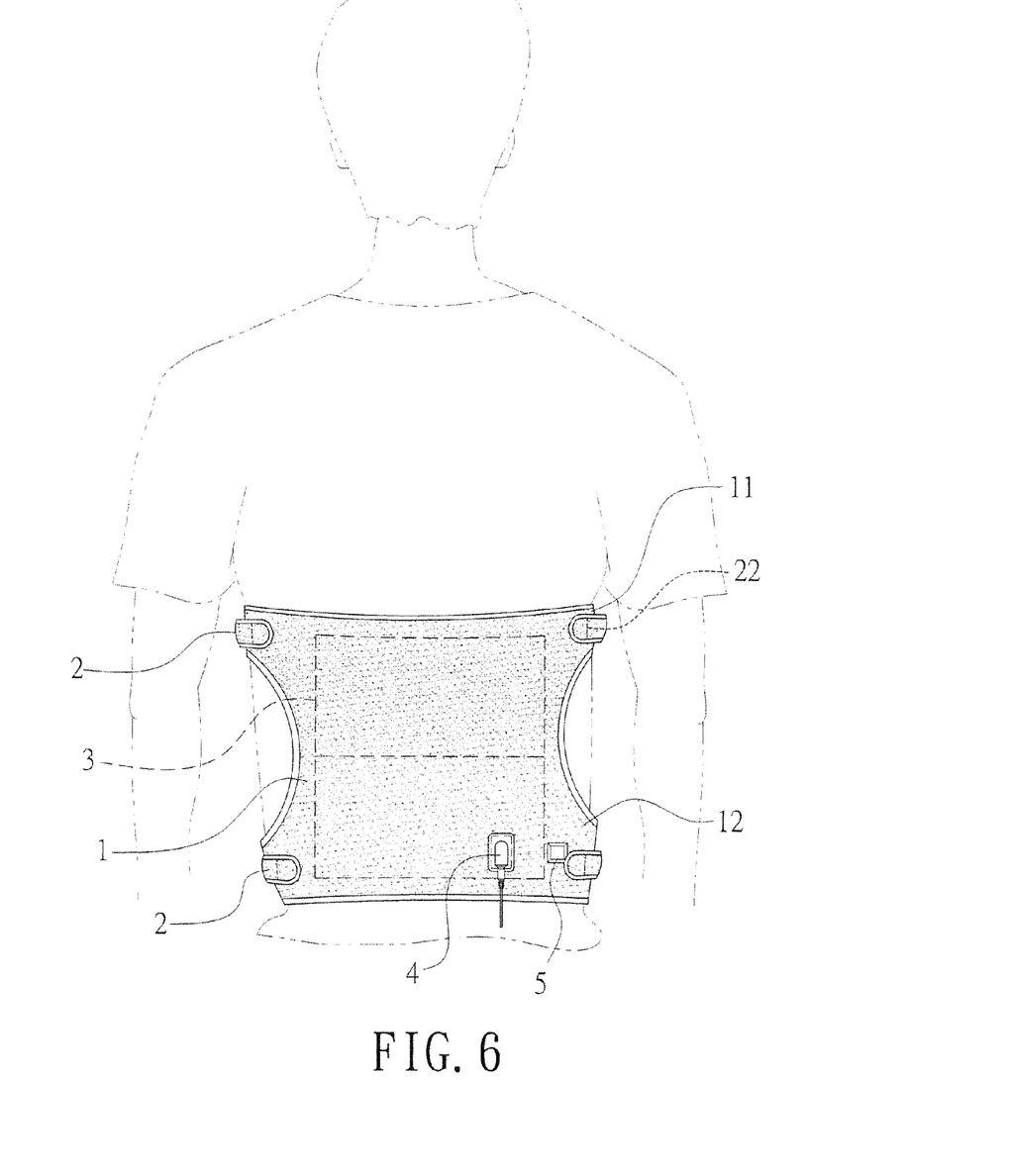
FIG. 6 shows that the heating pad assembly of the present invention is applied to the user's waist.

As shown in FIG. 6, when the heating pad assembly is used to the waist, the pad 1 is applied to the desired portion, the second loop pieces 22 of two respective ends of the two fastening strips 2 are connected to the first hook pieces 12 of the connection portions 11 at one end of the pad 1, and the two fastening strips 2 are wrapped to the waist and then the second loop pieces 22 of the other two respective ends of the two fastening strips 2 are connected to the first loop piece 13 of the pad 1.

Figure 7:
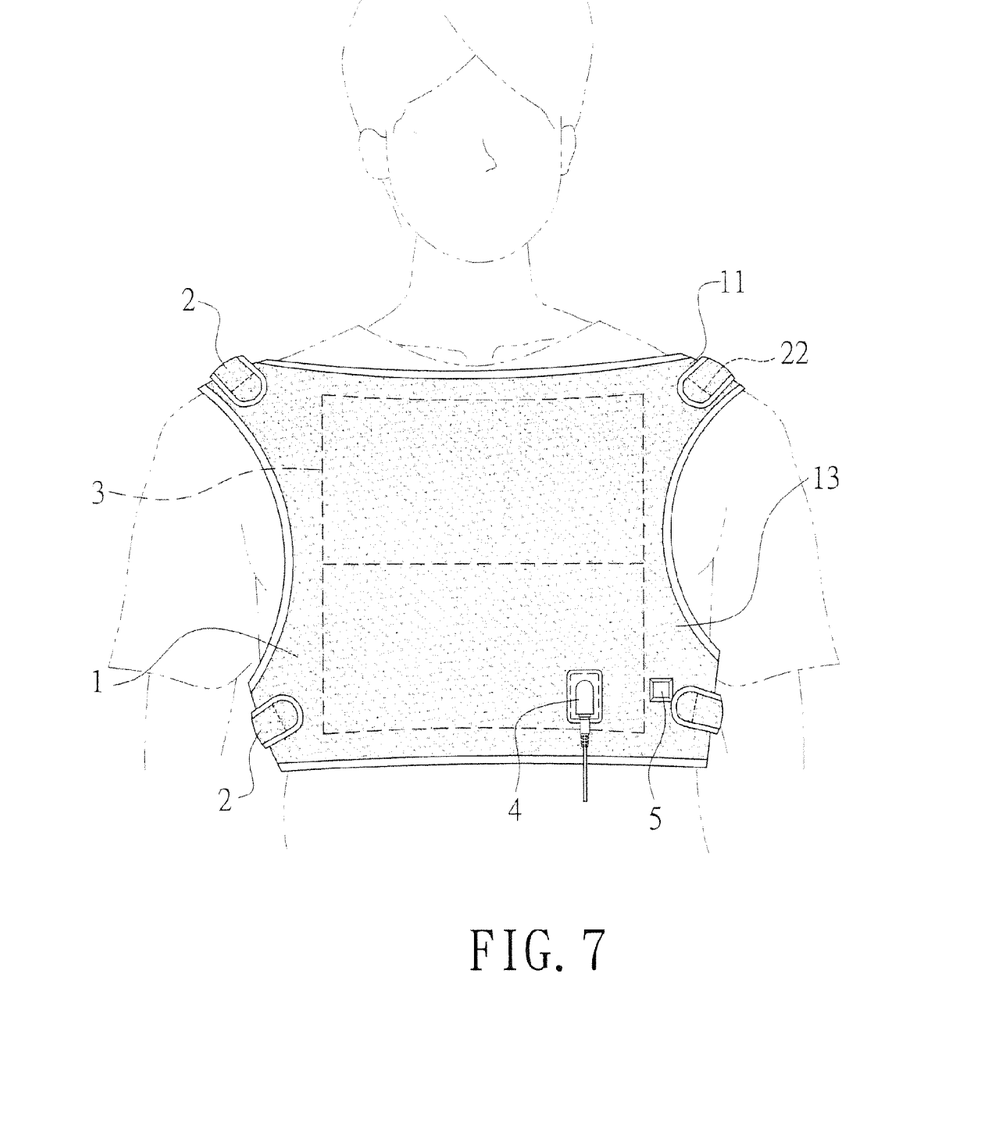
FIG. 7 shows that the heating pad assembly of the present invention is applied to the user's chest.
Figure 8:
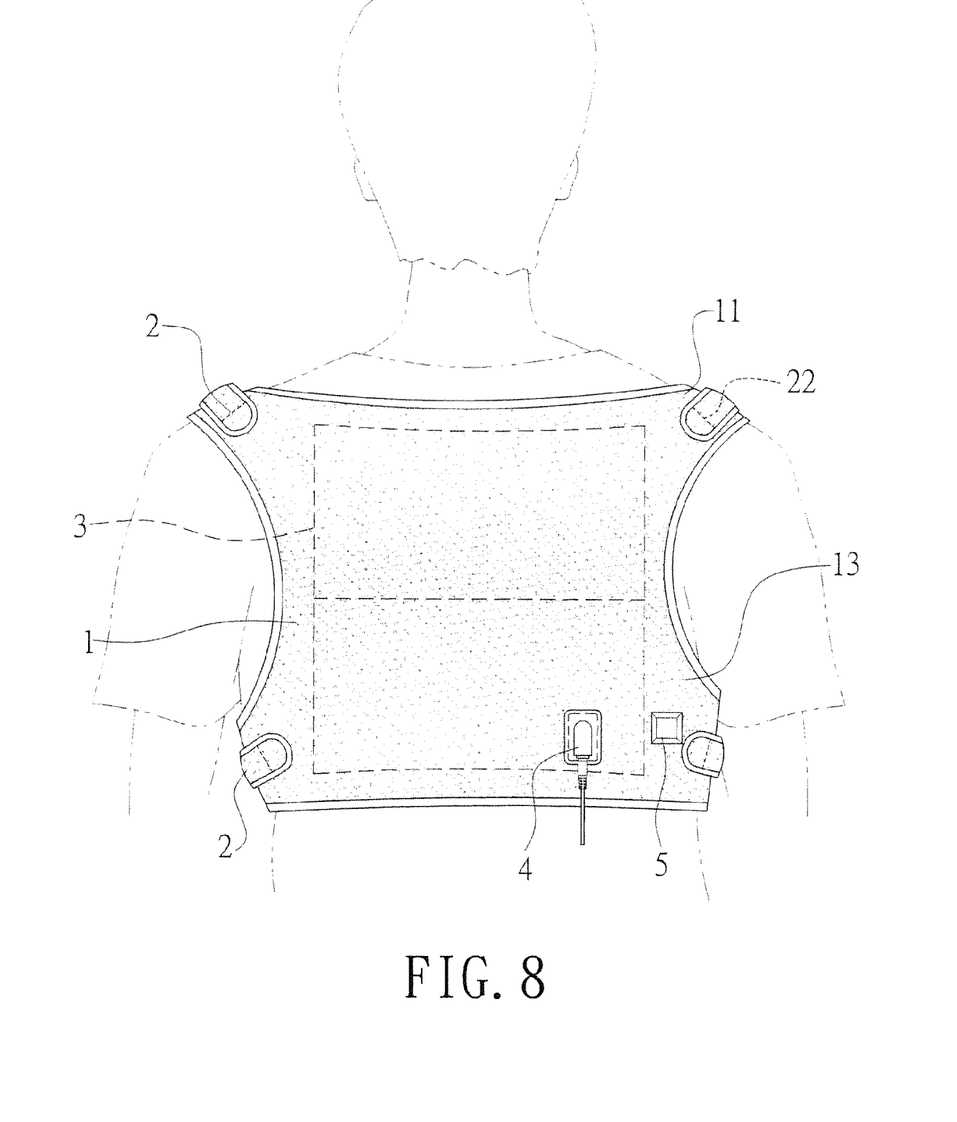
FIG. 8 shows that the heating pad assembly of the present invention is applied to the user's back.

As shown in FIGS. 7 and 8, when the heating pad assembly is used to the chest and the back, the pad 1 is applied to the desired portion, the second loop pieces 22 of two respective ends of the two fastening strips 2 are connected to the first hook pieces 12 of the connection portions 11 at one end of the pad 1, and the two fastening strips 2 are wrapped to around the shoulder and then the second loop pieces 22 of the other two respective ends of the two fastening strips 2 are connected to the first loop piece 13 of the pad 1.

Figure 9:
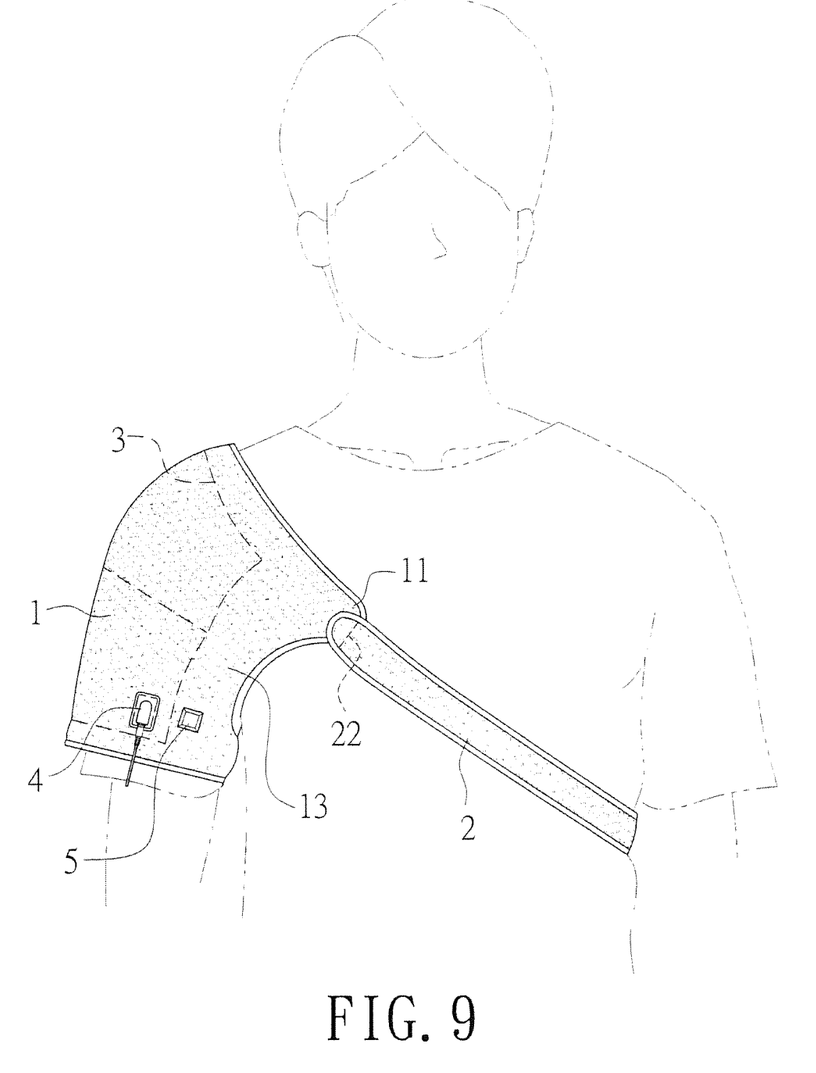
FIG. 9 shows that the heating pad assembly of the present invention is applied to the user's shoulder.

As shown in FIG. 9, when the applied portion is the shoulder, the pad 1 is applied to the shoulder, the first hook piece 12 of the connection portion 11 at one end of the pad 1 goes around the arm and then is hooked to the first loop piece 13 on the same end of the pad 1. A fastening strip 2 is used to hook the second loop piece 22 on one end thereof with the first hook piece 12 on the other end of the pad 1. The other end of the fastening strip 2 goes around the user's body and the second hook piece 21 of the fastening strip 2 is hooked to the first loop piece 13 of the pad 1.

Figure 10:
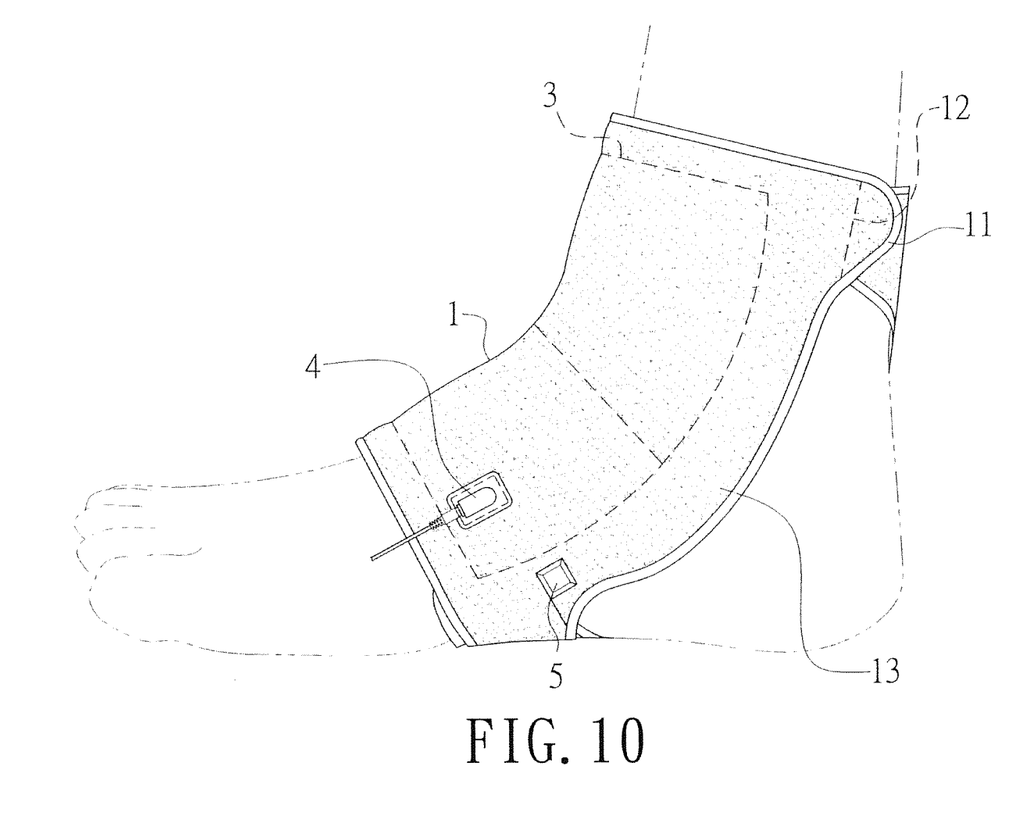
FIG. 10 shows that the heating pad assembly of the present invention is applied to the user's ankle.

FIG. 10 shows that the heating pad assembly is used to the ankle. The pad 1 is applied to the ankle. The first hook pieces 12 of the connection portions 11 at one end of the pad 1 are hooked to the first loop piece 13 on the other end of the pad 1.

The present invention can be used to any portion of the user's body by the pad 1 and the two fastening strips 2. The user simply prepare one pad 1 and two fastening strips 2, he or she can apply the heating pad assembly to arm, elbow, thigh, knee, chest, back, waist, shoulder and ankle.

Figure 11:
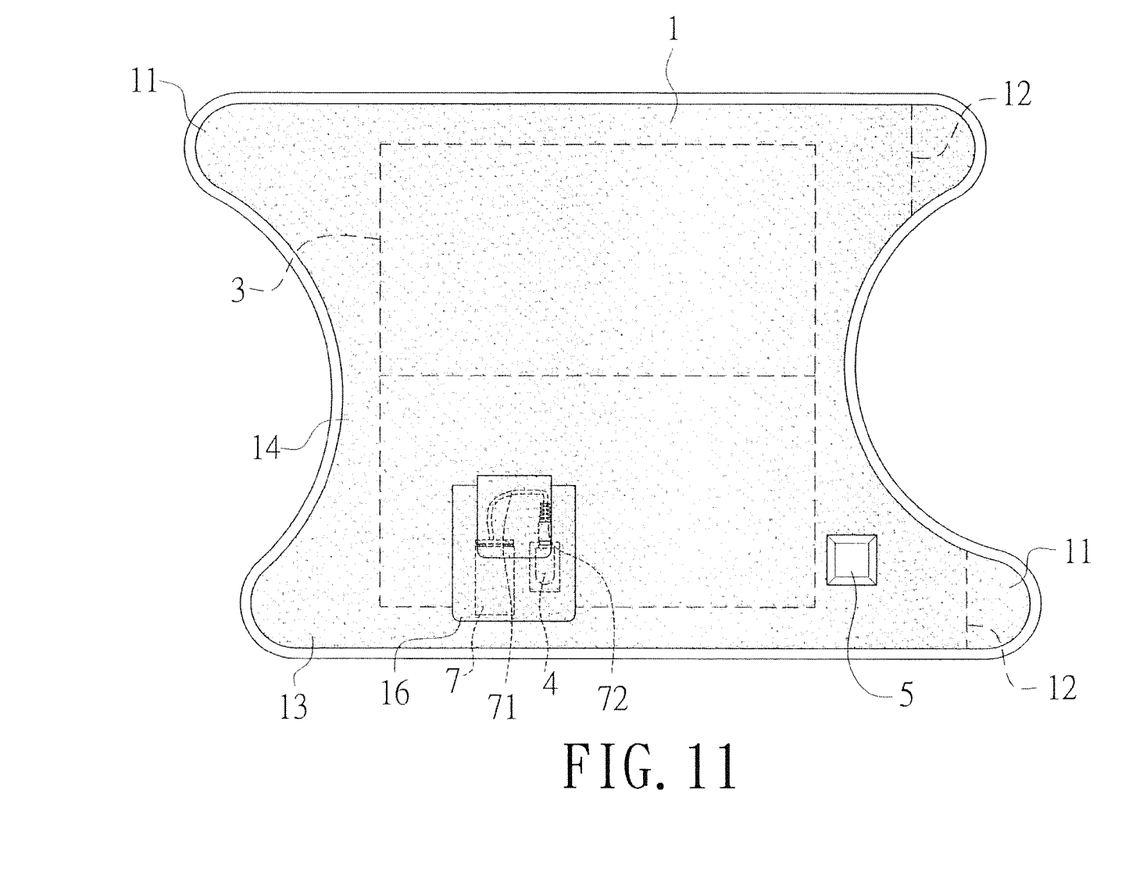
FIG. 11 shows another embodiment of the heating pad assembly of the present invention.

FIG. 11 shows another embodiment of the present invention, the pad 1 has a pocket 16 connected thereto, and a battery 7 and the receptacle 4 are located in the pocket 16. A wire 71 has one end electrically connected to the battery 7 and the other end of the wire 71 has a connector 72 which is connected to the receptacle 4. When the user presses the pressing portion 511 to activate the control unit 53 which adjusts the current generated from the battery 7 to the heating pad 3. The heating pad 3 generates heat to warm the user's body. The battery 7 allows the user to use the heating pad assembly without need of city electric power source, and the battery 7 is easily carried and portable so that the user can use the heating pad assembly without restriction.

While we have shown and described the embodiment in accordance with the present invention, it should be clear to those skilled in the art that further embodiments may be made without departing from the scope of the present invention.

What is claimed is:

1. A heating pad assembly comprising:
 a pad;
 a heating plate connected in the pad, and
 a receptacle connected to the pad, a first wire located within the pad and connected between the receptacle and a temperature control button unit which is fixed to the pad, a second wire located in the pad and connected between the temperature control button unit and the heating plate; and
 said temperature control button unit including a button located within the pad and a pressing portion protruding from a center of the button, the pad having an opening through which the pressing portion extends, the button sewed to the pad, a recess defined in a back of the temperature control button unit and located in a position opposite to the button, a control unit located in the recess and having a circuit board which has an operation button at a central portion thereof, a temperature display member located beside the operation button, a micro processing member connected to the circuit board and electrically connected to the operation button and the temperature display member, said second wire and a fixing member connected to the circuit board, the fixing member connected to a back of the button of the temperature control button unit so as to position the circuit board, the operation button and the temperature display member in the recess, said second wire connected to the circuit board extending beyond the fixing member.

2. The assembly as claimed in claim 1, wherein the pad has four connection portions extending from four corners of said pad and a recessed portion formed between the two connection portions on each of the two ends of the pad.

3. The assembly as claimed in claim 1, wherein the pad has a first hook piece on an inside thereof and a first loop piece connected to an outside of the pad.

4. The assembly as claimed in claim 3, further comprising a fastening strip which includes a second hook piece on an inside of said fastening strip and a second loop piece connected to an outside of the fastening strip, the second hook piece hooked to the first loop piece, the first hook piece hooked to the second loop piece.

5. The assembly as claimed in claim 1, wherein the receptacle has a body and a housing mounted to the body, the housing having a connection plate extending from a periphery of said housing and the connection plate sewed to the pad, the connection plate having a hole and the first wire extending through the hole and electrically connected to the body.

6. The assembly as claimed in claim 1, wherein the temperature control button unit has a transparent plate which is located in the recess and corresponding to the control unit, the transparent plate positioned in the recess by the fixing member.

7. The assembly as claimed in claim 1, wherein the pad has a pocket connected thereto and a battery located in the pocket, the battery electrically connected to the receptacle.

8. The assembly as claimed in claim 1, wherein the pad includes a pocket connected thereto, a battery and the receptacle located in the pocket, and the battery electrically connected to the receptacle.

9. The assembly as claimed in claim 8, wherein the pad includes a first hook piece on an inside thereof and a first loop piece connected to an outside of the pad, a fastening strip having a second hook piece on an inside thereof and a second loop piece connected to an outside of the fastening strip, the second hook piece hooked to the first loop piece, the first hook piece hooked to the second loop piece.

\* \* \* \* \*